(12) United States Patent
Lecomte et al.

(10) Patent No.: US 7,956,233 B2
(45) Date of Patent: Jun. 7, 2011

(54) SUPPORT SYSTEM FOR THE TREATMENT AND PREVENTION OF DISEASES OF THE VEINS

(75) Inventors: Serge Lecomte, Dijon (FR); Guy Dupasquier, Rivas (FR); Catherine Vermeulen, Saint Priest En Jarez (FR)

(73) Assignee: Laboratoires Urgo, Chenove (FR)

( * ) Notice: Subject to any disclaimer, the term of this patent is extended or adjusted under 35 U.S.C. 154(b) by 222 days.

(21) Appl. No.: 12/225,263

(22) PCT Filed: Mar. 23, 2007

(86) PCT No.: PCT/FR2007/050990
§ 371 (c)(1),
(2), (4) Date: Sep. 17, 2008

(87) PCT Pub. No.: WO2007/113430
PCT Pub. Date: Oct. 11, 2007

(65) Prior Publication Data
US 2009/0112145 A1  Apr. 30, 2009

(30) Foreign Application Priority Data
Mar. 24, 2006  (FR) .................................. 06 51025

(51) Int. Cl.
*A61F 13/00*  (2006.01)

(52) U.S. Cl. .......................................... 602/41; 602/76
(58) Field of Classification Search ............. 602/41–54, 602/75–76; 128/888–889
See application file for complete search history.

(56) References Cited

U.S. PATENT DOCUMENTS

| | | | | |
|---|---|---|---|---|
| 4,005,709 | A * | 2/1977 | Laerdal | 602/53 |
| 6,368,687 | B1 * | 4/2002 | Joseph et al. | 428/40.1 |
| 2004/0199096 | A1 | 10/2004 | Court et al. | |
| 2005/0192524 | A1 | 9/2005 | Lipshaw et al. | |
| 2007/0005037 | A1 * | 1/2007 | Mansfield et al. | 604/385.3 |

FOREIGN PATENT DOCUMENTS

| | | |
|---|---|---|
| EP | 0 878 179 A2 | 11/1998 |
| EP | 1 709 947 A1 | 10/2006 |
| WO | WO 00/42957 | 7/2000 |

* cited by examiner

*Primary Examiner* — Michael A. Brown
(74) *Attorney, Agent, or Firm* — Hamre, Schumann, Mueller & Larson, P.C.

(57) ABSTRACT

The present invention relates to a support system particularly intended for treatment and prevention of diseases of venous origin, characterized in that it comprises a first support layer, which is composed of an elastic band attached across its entire surface to an absorbent layer, and a second support layer, which is a self-adhesive elastic band. This support system has a dynamic coefficient of elasticity of between 5 and 55 Newton/cm.

15 Claims, 7 Drawing Sheets

SUPPORT SYSTEM FOR THE TREATMENT AND PREVENTION OF DISEASES OF THE VEINS

The present invention relates to a novel compression system for the prevention and the treatment of pathologies of venous origin.

This system consisting of two layers is simple and quick to apply.

The use of various compression systems has long been known for treating pathologies of venous origin, such as, for example, venous insufficiency, the treatment of varicose veins or leg ulcers, or even to prevent venous thrombosis.

This is because the application of a sufficient pressure acts favourably:
- on the one hand, at the level of vessels by reducing the calibre of veins, which leads to the acceleration of blood flow and to the re-establishment of the valve function; and
- on the other hand, at the tissue level by encouraging better oxygenation and a reduction of oedema.

In the treatment of chronic wounds and especially in that of leg ulcers, the use of a compression system that re-establishes or encourages a normal venous circulation is the reference treatment and the only therapy that has proved its effectiveness in caring for and avoiding the recurrence of this type of wound.

An effective compression system must be able to respond to four main objectives.

First, the system must be able to be worn continuously day and night for several days (for example, a week).

To this end, this system must therefore enable the simultaneous application of:
- on the one hand, a relatively low pressure called the "resting pressure" when the muscle is relaxed in order to be comfortable, and in particular bearable during the night; and
- on the other hand, a relatively high pressure called the "working pressure" when the muscle is tensed or during movements, and in particular when walking.

Second, the pressure difference between the resting pressure and the working pressure must be sufficient to encourage venous reflux.

Third, the values of the resting pressure, the working pressure and the pressure difference must be stable over time.

Fourth, the system must be simple and quick, and completely safe, to apply in order to avoid the risks of tourniquet if the pressure applied is too high or of ineffectiveness if the pressure or the pressure difference is too low.

To achieve these objectives, various systems using knitted or woven elastic bandages called compression bandages have been developed.

When being applied around a limb such as the leg, each bandage is stretched and according to the degree of elongation it applies a higher or lower pressure to the leg.

This pressure, which is the treatment pressure, depends mainly on two factors, the extensibility of the bandage and the circumference of the limb to which the latter is applied.

Elastic compression bandages are therefore wound around the leg with a given extension. While winding the bandage, the turns of latter overlap more or less completely. Very often, this overlap is 50%.

Manufacturers generally provide tables and product ranges that enable the pressure to be applied to be determined for a given limb diameter and the appropriate system to be chosen.

Compression bandages are classified very imprecisely by health professionals into two large categories.

1) Short Stretch Bandages

These bandages are intended to be applied with a low stretch (for example, often defined as less than 70% to 90%) and exert a low resting pressure and a high working pressure. They therefore have a large pressure amplitude, in particular during movements, for example when walking.

Short stretch bandages nonetheless have many drawbacks.

First of all, they are difficult to apply, as small variations in stretch during application generate a strong increase or decrease in the pressure attained. There is therefore a risk of tourniquet if the pressure applied is too high or a risk of ineffectiveness if it is insufficient.

Moreover, their low extensibility makes them difficult to handle (in particular on passing over the heel and winding on in spirals with a 50% overlap). In addition, being applied with a stretch close to the elastic limit of the bandage, i.e. close to the limit beyond which any additional stretching causes irreversible damage, the bandage often undergoes a significant deformation over the course of time, which leads to a risk of losing its elastic properties. This results in the need to change these bandages frequently and in a corresponding increase in the cost of treatment. Similarly, in the case of oedema in the course of treatment, the diameter of the limb diminishes during the oedema reduction phase and, to avoid any risk of tourniquet, these bandages must be replaced frequently.

2) Long Stretch Bandages

These bandages are easier to apply as they have better extensibility. Due to this fact, variations in stretch at application do not generate significant variation in the pressure applied. The risk of tourniquet is low.

Conversely, these bandages lead to small pressure variations between resting and working and to a small pressure variation in the course of movements, for example when walking.

They also cause some discomfort in the resting position if a high pressure is intended to be imposed, hence the need to remove them at night due to the discomfort caused.

These two categories of bandage are used alone or in association with a padding bandage intended to distribute pressure at the surface of the limb, and/or to protect bone projections due to its thickness, and to absorb possible exudates if the bandage is applied to an open wound, for example in the case of leg ulcers.

Long stretch bandages are marketed, for example, by the companies 3M, Thuasna and Smith and Nephew under the names Coheban®, Biflex® and Proguide® respectively.

Short stretch bandages in association with a padding bandage are marketed, for example, by the company Activa under the name Actico®.

Alongside these two compression systems, a compression system has been developed in Britain with four separate layers that are successively wound, one after the other, around the leg.

Such systems are marketed, for example, by the companies Smith and Nephew and Urgo Limited under the names Profore® and K4 respectively.

These four-layer systems comprise:
- a first inner padding layer which fulfils the same functions as previously described;
- a second layer which is a crepe bandage of very low elasticity which serves as an interface and flattens the surface of the padding layer;
- a third layer which is a highly elastic, i.e. long stretch, bandage, intended to apply part of the total pressure to the limb; and a fourth layer which is a highly elastic, i.e. long stretch, self-adhesive bandage, intended to apply the remaining pressure and to keep the whole system in place.

Theoretically, this system applies a low resting pressure, hence being without discomfort, a high working pressure and consequently an effective pressure difference.

However, the use of multiple layers makes this system uneconomical, very bulky and time-consuming to apply.

The use of the two latter layers, which are elastic bandages that have high extensibility, encourages safety against risks of tourniquet. Conversely, the application of these successive layers without true control of the extensibility makes the real effectiveness of the system during its employment uncertain. The increase in the number of layers also increases the risk of the system slipping. Finally, the variability of elastic properties inherent in their manufacture makes the real effectiveness of the system even more uncertain.

All the compression systems known to date aim mainly, through the action of one or more elastic bandages in association with absorbent padding, to apply a target pressure of 30 to 50 mmHg to the leg for an average ankle of 23 to 25 cm circumference, and to maintain these pressures over the course of time.

However, it appears that the notions of pressure difference and movement have not been studied by the manufacturers of these known products.

All these systems have been designed starting from a single principle whereby the applied pressure satisfies the formula defined by Laplace's law:

$$P = k\frac{2\Pi F}{C} \times n$$

in which:
P is the pressure expressed in mm of mercury;
F is the tensile force, expressed in newtons/cm, of the bandage at a given stretch;
C is the circumference, expressed in cm, of the limb on which the bandage(s) is (are) wound;
n is the number of turns formed by the bandage around the limb; and
k is a constant.

However, Laplace's law corresponds to a static mathematical model. Its use in working out or choosing an effective compression system therefore does not take account of the dynamic aspects connected with the evolution and the adaptation of the system depending on rapid variations in the circumference of the leg during movements. In vivo pressure measurements, carried out using pressure sensors positioned below a four-layer compression system, have shown that such a system can really provide an effective pressure difference during movements. However, it is not really known why and which are the characteristics that enable this result to be obtained.

Moreover, the known compression systems using a padding in association with one or more elastic bandages do not take into account the frictional and compressive forces being applied between these different layers, nor the variations in diameter that inevitably result from the successive application of different layers.

Various studies have shown that the total pressure exerted by the system is not proportional to the sum of the pressures exerted by each bandage. The inventors have also observed that the padding layer has a significant influence on the values of the pressure applied by a bandage.

If the application problems, which influence the effectiveness and innocuousness of the previously mentioned compression systems, are added to these dynamic stresses, there is therefore a very large uncertainty in the real performance of these systems, which doubtless explains the contradictory or disappointing results obtained during various clinical studies.

Several solutions have been proposed to attempt to improve compression systems. Thus patent documents EP 490 793, EP 671 898, EP 820 261, EP 876 809 and U.S. Pat. No. 3,613,679 may be cited, which describe calibration means allowing the application of elastic bandages to be made safer and easier.

In patent EP 460 040 an elastic bandage has also been described which provides a sufficient compressive force at low stretch, said compressive force remaining virtually constant even in the case of a large increase in stretch.

Finally, patent EP 651 628 describes a single-layer compression system resulting from the association of a self-adhesive elastic bandage and an absorbent layer in order to obtain a bandage that enables a permanent compressive force to be applied when it is stretched. The absorbent layer is intended to protect the wound by absorbing the compressive forces and to absorb the exudates.

However, the product described in this prior patent has many drawbacks.

If the padding covers the entire surface of the self-adhesive elastic bandage, this system alone is not able to stick. Similarly, if only part of the self-adhesive bandage is covered by the absorbent layer while winding the bandage around the limb, the risks of one layer slipping over the other, and consequently the risks of the applied pressure evolving over the course of time during movements, are increased. Inhomogeneous covering is a source of large variations in applied pressures.

Even if the use of such a compression system consisting of a single layer enables the influence of the padding layer to be reduced, it does not solve all the problems linked with obtaining an effective compression system that is simple to apply.

Under these conditions, it appears that none of the previously cited documents, nor any of the solutions described to date, envisages studying or evaluating the influence of the dynamic stresses linked with movements on the properties to be obtained in order to develop an effective compression system.

It is the approach to this problem that has produced the present invention, by determining the essential characteristics that an effective compression system and its constituent bandages must possess.

The object of the present invention is therefore to provide a compression system that enables the interference of the padding on the applied pressure to be eliminated, which responds to the dynamic stresses and to their consequences on the overall effectiveness during its use, which is simple to apply, comfortable and which maintains an effective pressure difference over the course of time.

In order to obtain such a system, the inventors have studied the variation in pressure differences between resting and working pressure, in particularly during movement, and their evolution over the course of time.

The inventors have thus analysed the properties of known compression systems by measuring, in particular, the pressures at application, the pressure difference during movements, the maximum (working) and minimum (resting) support pressures and their evolution over time.

In this way they have been able to demonstrate the properties of known short stretch systems, long stretch and multilayer systems, along with the significance of the padding layer, and to find the results reported for these products during in vivo clinical tests by measurements of pressure under the compression system.

Moreover, and surprisingly, the dynamic study of the viscoelastic properties of bandages has enabled the determination of a new physical characteristic, the dynamic elasticity coefficient, which is correlated with the pressure differences.

In fact, support bandages are made of viscoelastic materials, the technical characteristics of which result from the choice of their constituents, the yarns (denier, kind of fibres, covering), their textile construction (weaving, knitting) and additional treatments applied to them (steaming, incorporation of self-adhesive latex, adhesive coating, etc.).

The technical characteristics of these bandages are conveyed by their stress-strain curves, well known to experts in textile materials.

The relationship between the force (and hence the applied pressure) and the stretch of the bandage is illustrated by the graph representing a tensile force-elongation test on a bandage specimen using a tensile testing machine. This representation shows the various areas characteristic of the deformation of an elastic bandage and may be considered as the "identity card" of each bandage. The types of curves obtained using this test for various commercial products are thus shown in FIG. 1.

The inventors have studied, for the first time, the evolution of the characteristics of various compression systems and their constituents for a given stretch on the stress-strain curve, i.e. the dynamic evolution of these systems and of their constituents around an operating point. It is by studying this evolution that the inventors have revealed, in a quite unexpected and surprising manner, a dynamic characteristic (which they have called the dynamic elasticity coefficient) and that they have discovered that there is a correlation, for a given elastic bandage, between this characteristic and the pressure difference provided by this bandage, evaluated in vitro. In addition, it has been discovered that in the case of the superposition of two support bandages, the sum of the pressure differences of the system is virtually equal to the sum of the pressure differences generated by each bandage and that in addition the same addition phenomenon exists for the dynamic elasticity coefficients. This correlation is completely unexpected. This is because it links two experimental quantities obtained by testing methods that are completely different in principle. Furthermore, it holds for products with very different properties (stretch, elasticity) and textile structure (woven, knitted, latex-coated, etc.). Finally, despite the variations intrinsically linked with the manufacturing reproducibility of these elastic bandages and with the uncertainties in the measurements of pressure difference and of the dynamic elasticity coefficient, the correlations obtained are excellent.

Thanks to these elements, and after having eliminated interference introduced by the presence of a layer of independent padding by choosing a compression system in which this padding layer is linked to an elastic bandage, the inventors have been able to determine the characteristics which must be fulfilled by an optimized system having the novel form of a two-layer system, and by each of its layers, in order to be effective and simple to implement.

In other words, the studies undertaken by the inventors have made possible the development of a novel two-layer compression system which for the first time in the prior art enables all the previously mentioned problems to be solved.

The present invention therefore proposes a novel two-layer compression system characterized in that it comprises:
a first compression layer consisting of an elastic bandage linked over the whole of its surface with an absorbent layer and which has a dynamic elasticity coefficient of between 1 and 45 newtons/cm; and
a second compression layer consisting of a self-adhesive elastic bandage that has a dynamic elasticity coefficient of between 1 and 45 newtons/cm;
the dynamic elasticity coefficient of the system being between 5 and 55 newtons/cm.

According to one preferred embodiment of the present invention, each layer of the two-layer system has a tension set for a stretch at which it is applied of less than 10%.

According to another preferred embodiment of the present invention, each layer of the two-layer system comprises a calibration means in order to apply said layer with sufficient stretch.

According to a second aspect, the present invention includes a compression kit that consists of the two-layer compression system defined above and a calibration system in order to calibrate at least one of the two compression bandages before use.

DETAILED DESCRIPTION OF THE INVENTION

The invention will be better understood and other characteristics will appear more clearly on reading the following explanatory description with reference to the appended drawings in which.

Figure 9:
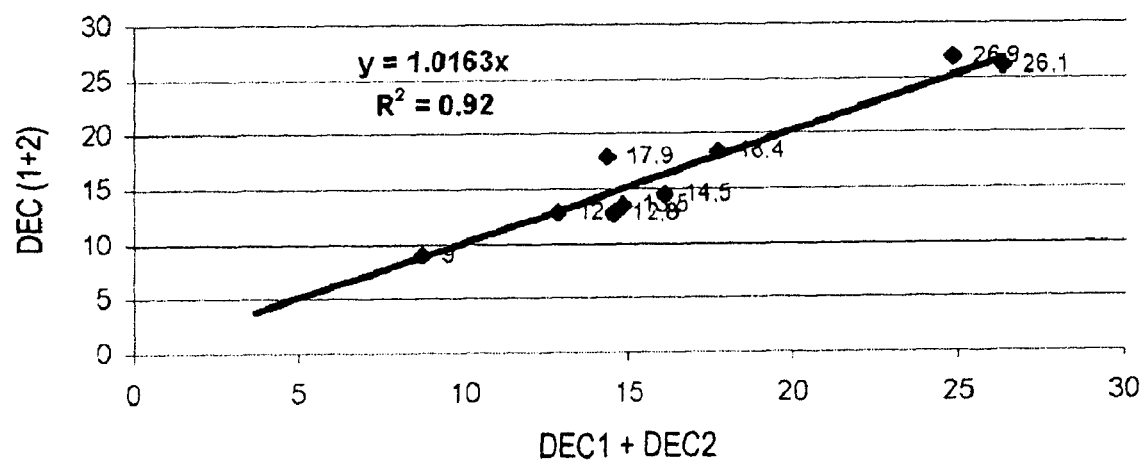
Figure 10:
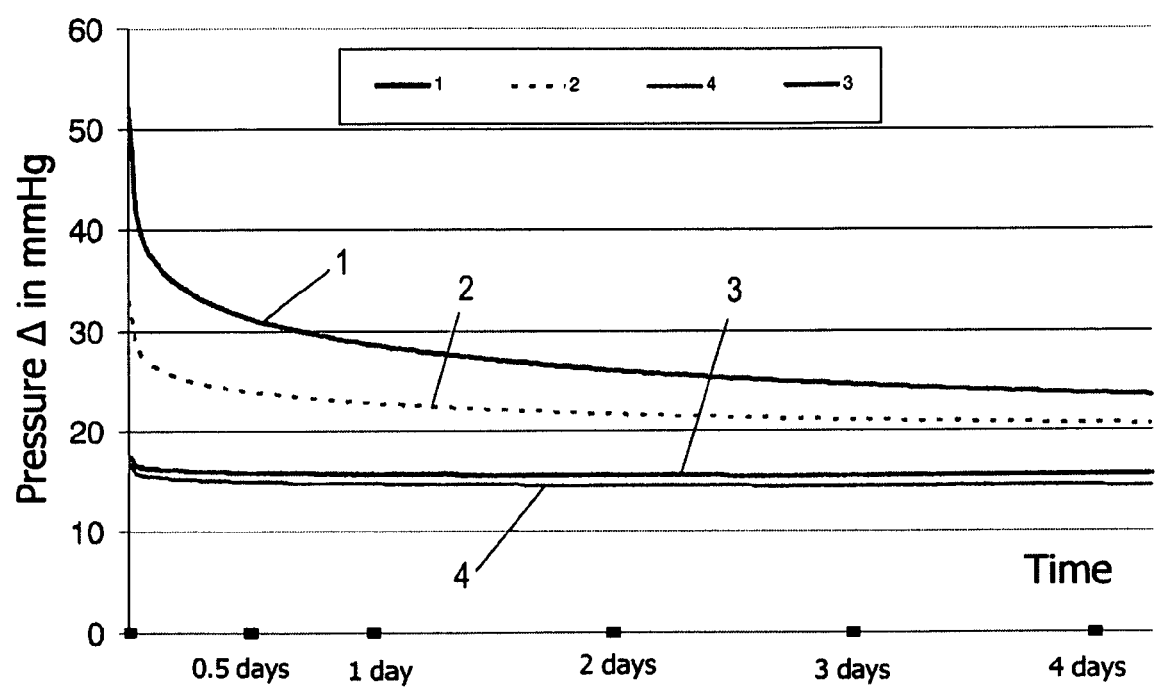

FIG. 9 illustrates the correlation between the sum of the DECs for each bandage constituting a compression system and the DECs of corresponding compression systems according to the invention; and FIG. 10 illustrates the evolution over the course of time, expressed in days, of the pressure difference Δ (expressed in mm of mercury) for the products Actico® (padding+self-adhesive bandage applied at its maximum stretch) (curve 2); Profore® the four layers of which are respectively applied at a stretch of 0% (padding), 35%, 50% and 50% (curve 4) and for the two compression systems consisting of the following elements Ex2-40%+Ex4-50% (curve 3) and Ex1-30%+Ex6-90% (curve 1).

Figure 11:
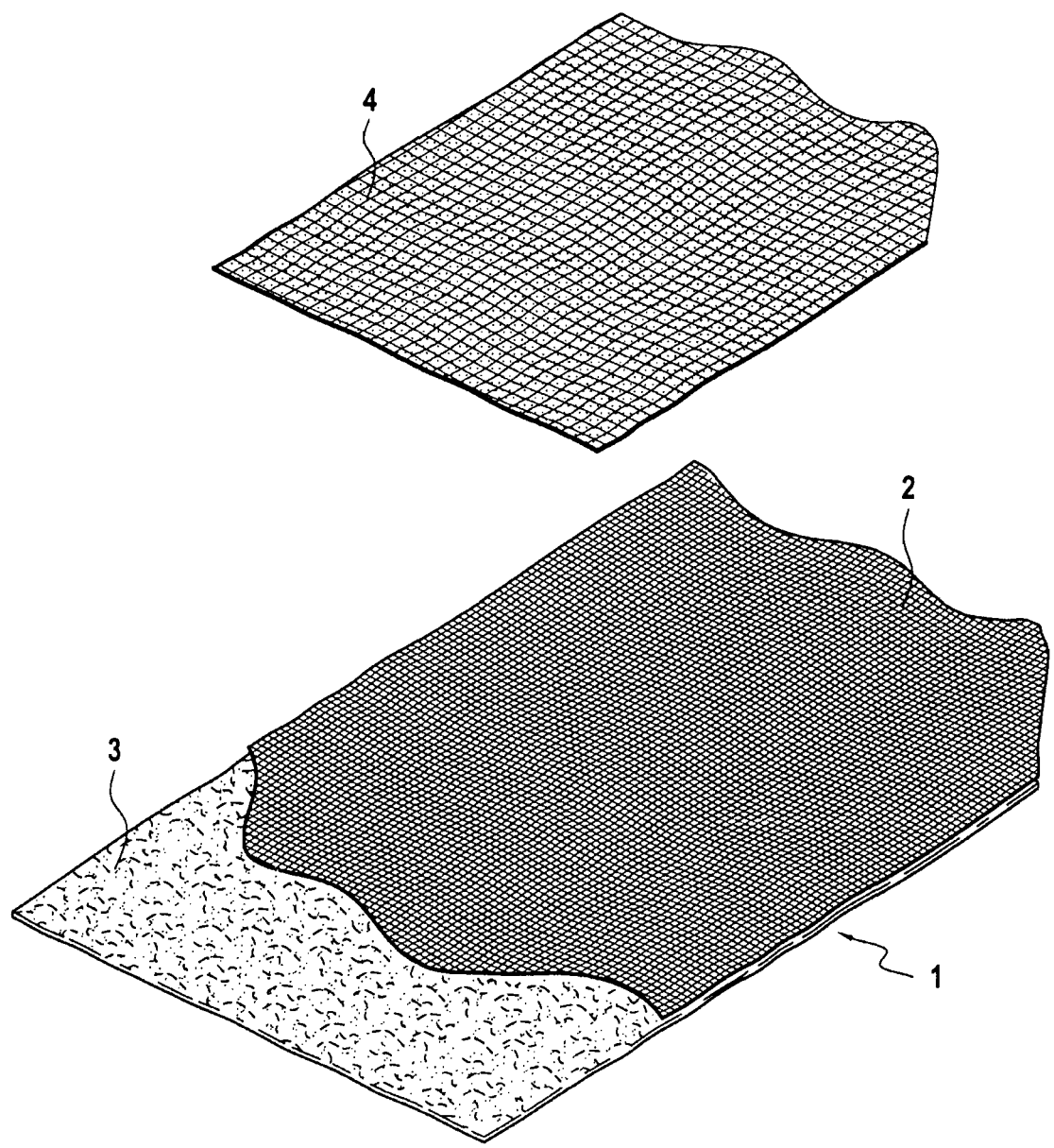

FIG. 11 illustrates a first compression layer 1 consisting of an elastic bandage 2 linked over the whole of its surface with an absorbent layer (a padding) 3, and a second compression layer 4 consisting of a self-adhesive elastic bandage.

By eliminating the role of the padding and thanks to the choice of dynamic elasticity coefficient for each bandage and for each compression system in its entirety, the present invention provides care staff with an effective solution that is simple to employ and comfortable for the patient, enabling all pathologies linked with venous insufficiency to be treated. Furthermore, by varying mainly the dynamic elasticity coefficients, and secondarily the tension set of the bandages used and the calibration possibilities, the present invention offers, for the first time in the prior art, the possibility of adapting the choice of the two layers constituting the compression system to the duration of the treatment, and to the severity of the pathology, particularly in the presence of oedemas or leg ulcers for example. In all cases, this adaptation is reflected in appreciable gains in terms of application time, and hence costs, and in improved safety in the application as the determination of the DEC enables the uncertainty linked with the reproducibility of the elastic and dynamic properties of the bandages used to be removed. The great flexibility in the association of the two bandages which results from the present invention thus enables adaptation to multiple situations.

The possibility of dividing the pressure difference over the two bandages in fact guarantees the possibility of completely safe adjustment of compression systems offering a wide range of pressure differences. A pressure difference of between 15 mm and 25 mm of mercury is generally considered necessary to re-establish correct venous flow. However, depending on the pathology, whether it is a treatment on legs without a serious ulcer or a difficult treatment on legs badly damaged with oedema, this range of values may extend from 10 to 35 mm of mercury, or even from 10 to 40 mm of mercury. The invention allows, for example, application on one healthy leg of a higher working pressure and pressure difference to the extent that the risks of tourniquet or the risks of damaging leg tissues are lower than with the known systems, all the more so as the application is simple.

One of the objectives of the present invention is to provide a compression system ensuring a pressure difference preferably of between 15 and 25 mm of mercury, or even between 10 and 35 mm of mercury, or again even between 10 and 40 mm of mercury if necessary.

To achieve this objective, it is hence possible to vary the dynamic elasticity coefficient of each bandage so as to obtain a compression system having a dynamic elasticity coefficient that varies between 5 and 55 newtons/cm.

Preferably, a compression system that has a dynamic elasticity coefficient between 10 and 35 newtons/cm, and more particularly between 15 and 30 newtons/cm, will be used. In this latter range of values it has been observed that a pressure difference is obtained which quickly stabilizes and hardly evolves or does not evolve over the course of time.

To achieve these dynamic elasticity coefficients, the first and second layers of the compression system according to the invention will be formed of bandages with a dynamic elasticity coefficient of between 1 and 45 newtons/cm, preferably between 3 and 30 newtons/cm, and more preferably between 5 and 25 newtons/cm.

According to one preferred embodiment, in order to facilitate the application of the bandages that form the two layers of the compression system and to obtain a stable pressure difference quickly and over the course of time, bandages will be used that additionally have a tension set, measured for their stretch on application, of less than around 10% and preferably between 4 and 8%.

Such an embodiment is particularly suitable in the case of pathologies that are usually difficult to treat.

It has in fact been observed that such bandages are simpler to apply, in particular if their extensibility is low or for a stretch close to the elastic limit. In addition, it has been observed that after application such bandages undergo a very small loss in pressure and in pressure difference over the course of time. The risks of discomfort on application are hence reduced. With such bandages the working pressure, resting pressure and pressure difference values required are obtained from application onwards. It has been determined that for bandages having a tension set of less than 10% these values hardly evolve, or even do not evolve, over the course of time if the tension set is between 4 and 8%.

According to another preferred embodiment, in order to encourage precise application by the care staff, one or each bandage forming the compression system of the present invention will be provided with a calibration means.

This calibration means may be visual, such as for example a set of regularly spaced pictograms printed on the bandage, or produced using a calibration system, such as for example a stencil, by the care staff who are provided with information on the recommended stretch on application. This type of stencil or the explanations necessary to manufacture it may be incorporated in a kit that includes the two support bandages that form the compression system or a selection of support bandages that allow various suitable compression systems to be produced.

The principle of calibration using a stencil is the following.

The stencil is generally produced by means of a cardboard sheet in which an opening has been cut that may have, for example, an ellipsoidal or rectangular shape, allowing, as will be understood, a pictogram of the same shape to be produced on the bandage.

The transformation of these pictograms into circles or squares under the effect of stretching the bandage thus allows the latter to be calibrated. This principle is described, for example, in U.S. Pat. No. 3,613,679.

The rectangular shape, which is easiest to cut in a cardboard sheet, is preferably used.

The length and the width of the rectangle are mathematically determined depending on the stretch at which the bandage is intended to be applied. Hence if E is the stretch of the bandage on application and L the length of the rectangle that will be parallel in the weft direction of the bandage (i.e. perpendicular to the length direction of the bandage), the width La of the rectangle will be $$\frac{L}{1+E}.$$

For example, to calibrate a bandage that is intended to be applied with a 55% stretch, a rectangle having a length of 4 cm and a width of 4/(1+0.55) or 2.58 cm will be used.

To calibrate the bandage, rectangles of 4 cm length and 2.58 cm width are cut into a cardboard stencil. This stencil is positioned on the flat, unstretched bandage and the outline of this rectangle is drawn on the bandage, for example using a felt-tip pen.

In the context of the present invention, the use of bandages precalibrated during manufacture using pictograms in the shape of ellipses that transform into a circle at the desired stretch will be preferred. Advantageously, a compression system will be used of which the two constitutive layers are calibrated.

One of the main advantages of the present invention is to provide, in so far as they fall within the dynamic elasticity coefficient range, a wide choice of usable bandages to obtain an effective compression system.

An absorbent elastic bandage that can be used as a first layer in the compression system of the present invention can be manufactured according to techniques well known to the person skilled in the art. The production of such products is, for example, described in patent EP 651 628 in which a self-adhesive elastic bandage and an absorbent layer are combined.

In the context of the present invention, it is unnecessary for the elastic bandage to be necessarily self-adhesive. It need not be self-adhesive, or it may even be self-adhesive only on one side, for example that facing the absorbent layer.

The absorbent layer may be fastened onto the elastic bandage by any known means to produce the first layer of the compression system according to the invention. It must, however, cover the entire surface of the elastic bandage.

Various textile technologies, such as, for example, basting or needling, ultrasonic welding, lamination or fixing using an adhesive, may be used to produce this first layer.

In the context of the present invention it will be preferred to use an absorbent layer consisting of a padding and to fix the latter to the elastic bandage either by needling or using an adhesive. This adhesive may, for example, be a latex of the same kind as that which serves to stick the elastic bandages to make them self-adhesive or an acrylic adhesive.

Among the absorbent layers that can be used in the context of the invention it is possible to cite, for example, foams, such as polyurethane-based or olefin-based foams, or woven or non-woven textile materials based on synthetic or natural fibres, such as for example paddings.

In the context of the present invention the use of woven or non-woven fibre-based textile materials, which have better conformability than foams, will be preferred as an absorbent layer.

Because of their discontinuous structure, due to the assembly of fibres, these textile materials have a deformable surface which enables them to adapt to the curves and to the projecting parts of limbs to be covered better than foams which have a more rigid continuous plane surface.

Similarly, because of their discontinuous structure, textile materials generally have a greater water vapour permeability than foams for equivalent thicknesses.

By way of example, these paddings may consist of viscose fibres, polyester fibres, polyurethane fibres, cotton fibres, rayon fibres, etc.

Such paddings are, for example, the products marketed by the companies Urgo Ltd., Activa or Smith and Nephew under the names K-soft®, Flexi-ban® and Soft-ban® respectively.

In the context of the present invention, the K-soft® padding will especially be preferred, which consists of a mixture of 60% viscose fibres and 40% polyester fibres.

If there is a desire to increase the absorption capacity of the absorbent layer, paddings based on super absorbent fibres are advantageously used. Such paddings are, for example, described in patent EP 0 873 097.

The absorbent layer may optionally contain active agents which help to improve the healing of leg ulcers or which allow the pain or the oedema to be reduced, or even antibacterial agents.

According to a variant embodiment, it will be possible to introduce antibacterial fibres, for example silver fibres, into the padding, or to impregnate this with an antibacterial agent, for example Triclosan.

According to another variant embodiment, it will also be possible to deposit an antibacterial agent, such as a silver-based compound for example, on the surface of the absorbent layer or on the entire first surface of the system (absorbent layer-elastic bandage).

Any type of elastic bandage may be used for the manufacture of the first layer of the compression system according to the invention, whether woven, non-woven or knitted. However, a woven fabric will be preferred.

In the context of the present invention, the elastic bandage-absorbent layer assembly forming the first layer must, however, have the essential characteristic that enables an effective compression system to be obtained, namely a dynamic elasticity coefficient of between 1 and 45 newtons/cm.

This is because below 1 newton/cm this first layer does not provide any pressure or pressure difference. It then gives the system behaviour equivalent to that of a padding.

Beyond 45 newtons/cm, it has been observed that the force it is subjected to is very high and the pressure it exerts reduces very quickly, like the initial pressure difference, whatever the nature of the second layer. It has in fact been observed that the presence of the second layer does not modify the behaviour of the first layer, if this has a dynamic elasticity coefficient that is too high, and vice versa. Even if such a bandage reaches an equilibrium at the end of several hours in terms of applied pressure and pressure difference, the risk of imposing a pressure that is too high at the start and of a drop in pressure of the system over the course of time is too great.

The second layer of the compression system according to the invention consists of a self-adhesive elastic bandage that has a dynamic elasticity coefficient between 1 and 45 newtons/cm.

A self-adhesive elastic bandage used as a second layer may be varied in nature.

Generally speaking, elastic bandages that are coated with natural rubber latex or with adhesives having a low adhesion will be used.

The production of such bandages is well known to the person skilled in the art.

The latex is preferably deposited on both sides of the elastic bandage in an amount of around 0.01 to 75% by weight so as to provide an elastic bandage that adheres to itself without adhering to the skin or to clothes. In the context of the present invention, latex coatings of around 25 to 33 $g/m^2$ will be preferred.

Various types of textile construction that might be used to produce self-adhesive elastic bandages are, for example, described in patent EP 651 628.

Methods enabling the deposition of latex or low-adhesion adhesives onto elastic bandages are described, for example, in U.S. Pat. No. 4,699,133 et FR 2 611 756.

Self-adhesive elastic bandages marketed, for example, by the companies 3M, Activa, Urgo Ltd and Smith and Nephew under the names Coheban®, Actico®, Ko-flex® and Profore 4® can also be used in the context of the present invention.

Methods for evaluating the properties of a compression system according to the invention and for determining the essential characteristics that bandages constituting it must meet will now be described.

It has been possible to study the dynamic properties of compression systems in vitro due to the development of specific equipment.

Figure 2:
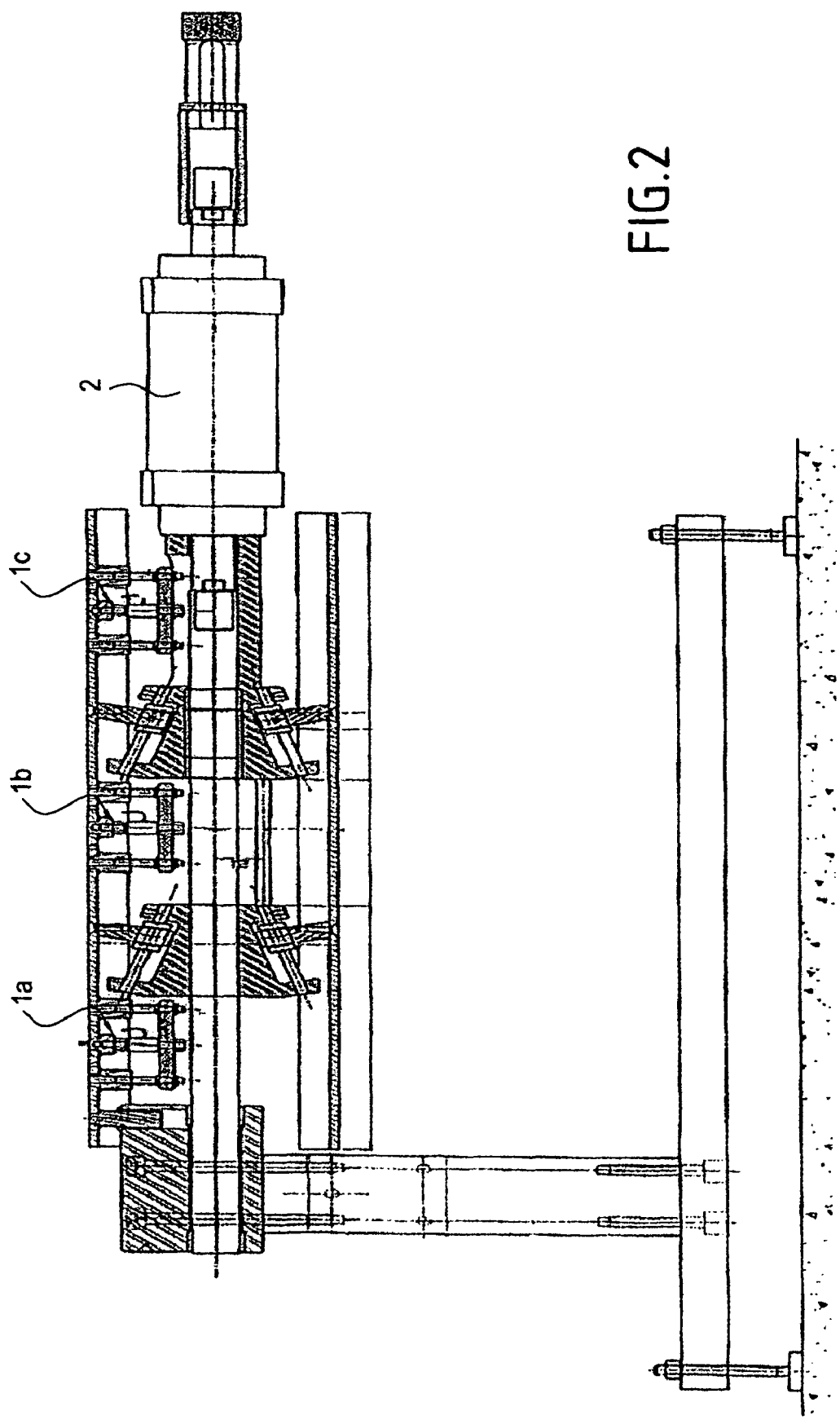
FIG. 2 is a cross-sectional view illustrating apparatus for measuring the pressure and the pressure difference in vitro.

Its principle is the following:

On a cylindrical device such as illustrated in FIG. 2, a succession of cycles is applied which consist in varying the circumference of the cylindrical device with an amplitude and a speed that can be parameterized.

The variation in circumference is controlled by a pneumatic system. The frequency of the cycles is linked with the parameterization of the pneumatic system. The level of variation in circumference chosen is around 3%, which corresponds to the value of the mean deformation of the circumference of the leg muscle when it contracts. A series of three strain-gauge sensors (1a, 1b, 1c) is fastened to the device and proceeds to measure pressures in real time. All this data is transmitted via an acquisition program to a computer where subsequent processing can be carried out.

The device generally consists of four identical, smooth, curved, steel plates arranged in a cylinder. These four plates are joined to two conical compression systems, one of which is stationary and the other of which can be moved in translation under the action of an actuator (2) operated by a pneumatic system.

Under the action of the actuator, the two conical compression systems return a translational movement that enables the four plates to move a proportional distance away from the axis, this distance being set by a control fixed at the end of the actuator.

Three openings are provided in one of the four plates, in which openings three XTFC (tension/compression) strain gauge sensors, marketed by the company Doerier, are housed, to which a flush surface of the same curvature as the plate has been fixed. The technical characteristics of these sensors are:

Range 0-10 newtons, linearity ≦0.5% of the maximum extension

Hysteresis ≦0.5% of the maximum extension.

The electronic sensors are conditioned for and connected to a three-channel data logger developed by the company Doerler with an analogue-digital converter which communicates through a program with a computer for tracking over time and for data processing.

This cylinder has a minimum perimeter of 35.9 cm and a maximum perimeter of 37 cm, which corresponds to a mean deformation of 3% chosen to correspond to the mean variation in circumference of the leg between resting and working and when walking. In order to get closer to reality, the bandage is applied at 75% of this deformation at t=0, that is on a cylinder that has a circumference of 36.2 cm. This is because during application of a bandage the leg is not completely at rest. The system is calibrated by statically calibrating sensors using a rigid bandage from which two weights have been suspended. To carry out these measurements, the compression systems and bandages are wound around this cylinder with a single covering of 100% for the tests subsequently carried out.

A length of bandage necessary to obtain this covering is cut. In the case where a single bandage that is not self-adhesive is tested, the latter is fixed at the desired stretch with the aid of an adhesive strip. The application at the desired stretch may also be made easier by the presence of a calibration means in the form of pictograms on the bandage.

In order to optimize the application conditions further, the following method is additionally used.

The apparatus has four graduated markers spaced apart by a distance $d_1$ equal to the perimeter of the cylinder at application (36.2 cm) divided by 4, or 9.05 cm. A template is manufactured on a rigid sheet having graduations spaced apart by a dimension $d_2$ such that if E is the stretch on application of the bandage, the graduation $d_2$ is such as to satisfy the equation $d_2=d_1/(1+E)$. The markers $d_2$ of the template are transferred to the bandage at rest. The bandage is then applied to the apparatus in such a way that the markers transferred to the bandage coincide with those ($d_1$) present on the apparatus. In this position the stretch is that desired since $$E = \frac{d1 - d2}{d2}.$$

Figure 1:
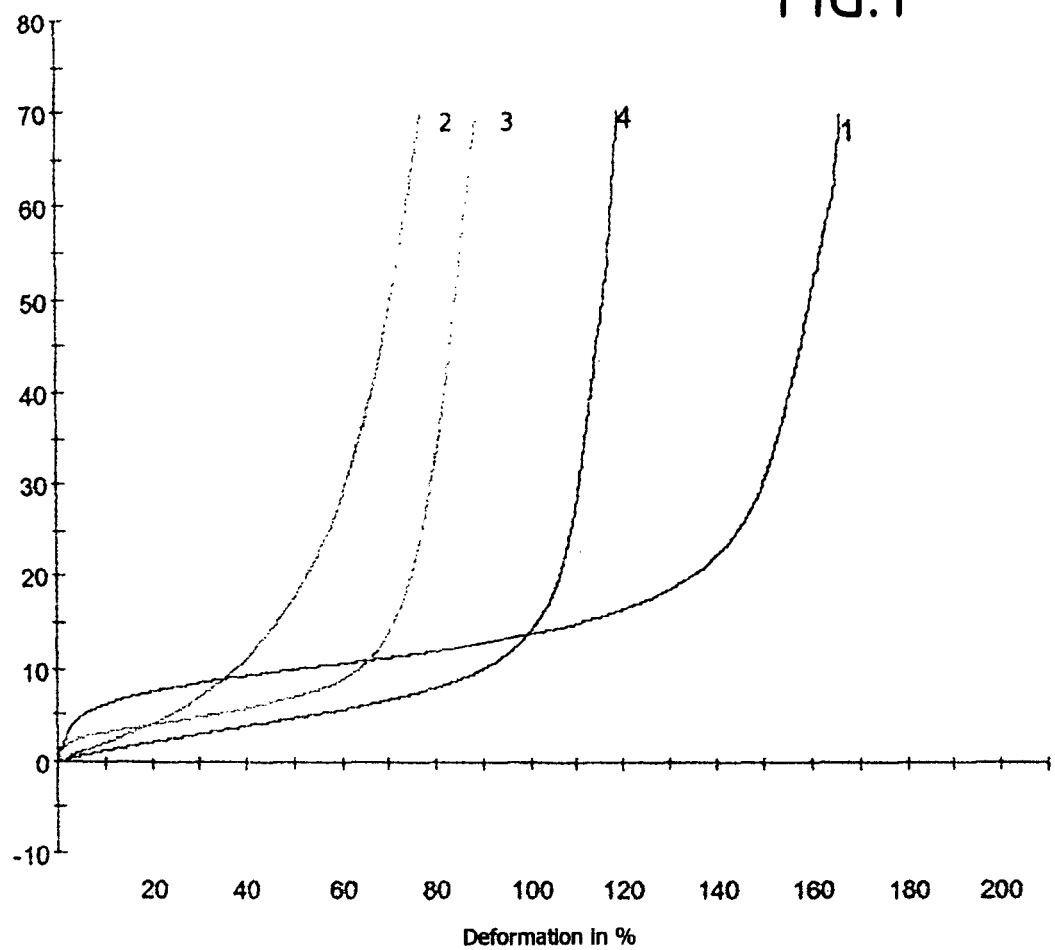
FIG. 1 shows the stress-strain curves of four known products, marketed by the companies Thuasna, Activa and Smith and Nephew under the names Biflex® 16 (3), Actico® (2), Proguide® (1) and Profore 4® (4) respectively.
Figure 3:
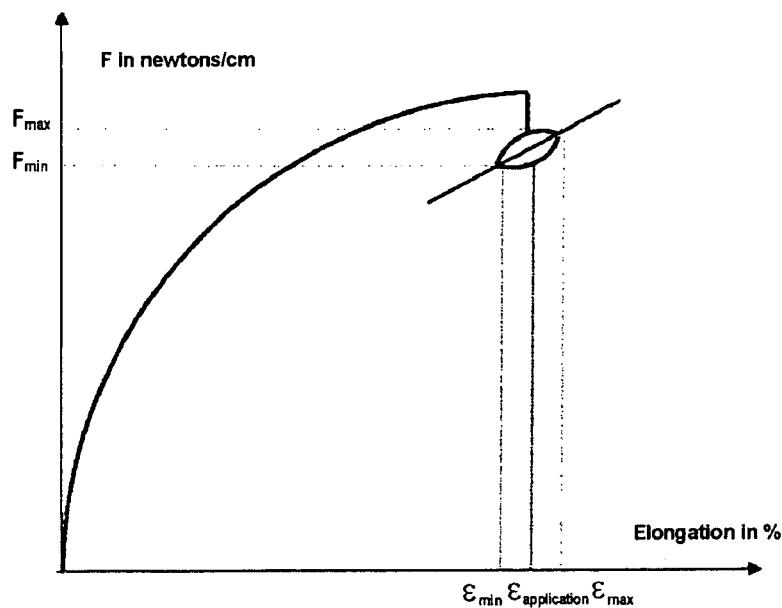
FIG. 3 illustrates the principle of measuring the dynamic elasticity coefficient of a bandage.

Measurement of the dynamic elasticity coefficient is carried out according to the following method, the principle of which is illustrated by FIG. 3.

The test protocol consists of a series of tensile load/unload cycles in the proximity of a given extension (deformation $\epsilon_{application}$) and of low amplitude (a few percent) around this point (variation: $\epsilon_{max}-\epsilon_{min}$).

In the tests that have been carried out, the variation was fixed at 3%.

The implementation of the test is carried out on a tensile testing machine which is an electronic dynamometer, for example an MTS brand dynamometer, equipped with a 100 newton load cell. The bandage is conditioned for 24 hours at 21±2° C. and at 60±15% relative humidity. The test is carried out under the same conditions. A bandage sample of 10 cm width and of 20 cm length is cut to carry out the test. In order to avoid the uncertainties in measurements linked with the relaxation of textile materials after cutting, the bandage specimen is allowed to stand for 10 minutes before carrying out the measurement. The specimen is then mounted between the jaws of the electronic dynamometer, then stretched to the extension at application ($\epsilon_{application}$) at a rate of 500 mm/min. A relaxation period of 30 seconds precedes a series of five load/unload cycles of amplitude $\epsilon_{max}-\epsilon_{min}$ around this point at the rate of 100 mm/min. By definition, the dynamic elasticity coefficient, hereafter denoted DEC, is the result of the following equation:

$$DEC = \left(\frac{F_{max} - F_{min}}{\epsilon_{max} - \epsilon_{min}}\right)_5$$

This coefficient is measured at the end of the fifth cycle.

It is expressed in N/cm.

$F_{max}$ and $F_{min}$ are the forces corresponding to the variations in stretch $\epsilon_{max}$ and $\epsilon_{min}$.

One of the advantages of this technique is that it also enables experimental determination of the DEC on a pair of bandages.

It has been observed that the DEC equivalent to a pair of bandages is equal to the sum of the DECs of each bandage. This relation is also experimentally verified if the two bandages are stressed at different degrees of extension. In this case, the two bandages are both kept in the jaws of the dynamometer, but the bandage which is stressed at the lowest extension is inserted in the jaws of the dynamometer with a greater initial length.

Figure 4:
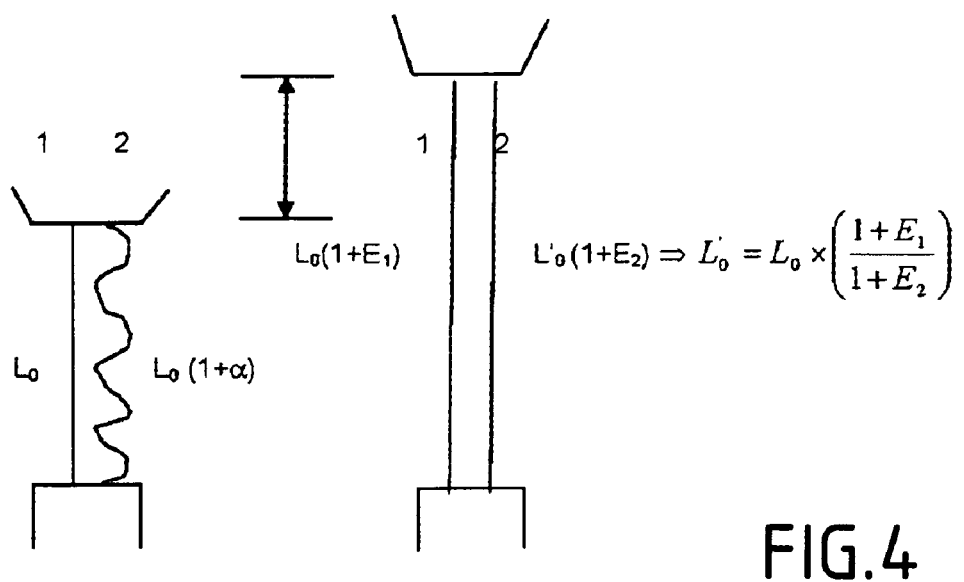
FIG. 4 illustrates the principle of measuring the dynamic elasticity coefficient of a system of two support bandages according to the invention.

The measurement of the DEC of two bandages, the principle of which is illustrated in FIG. 4, is carried out in the following manner.

In this figure, $L_0$ represents the initial length of the specimen of a first bandage intended to be stretched with a degree of stretch $E_1$.

Similarly, $L'_0$ represents the length of the specimen of the second bandage intended to be stretched to a degree of stretch $E_2$, which is less than $E_1$.

Knowing the degrees of stretch $E_1$ and $E_2$, it is easy to determine the length $L'_0$ of the specimen of the second bandage, the latter satisfying the following formula:

$$L'_0 = L_0 \times \left[\frac{1+E_1}{1+E_2}\right]$$

For example, in order to stress, in parallel, two bandages intended to be stretched to stretching degrees of 50% and 40% respectively, a specimen of length $L'_0=214$ mm will be used for the bandage intended to be stretched to 40% if a specimen of length $L_0=200$ mm is chosen for the bandage intended to be stretched to a degree of stretch of 50%.

Figure 5:
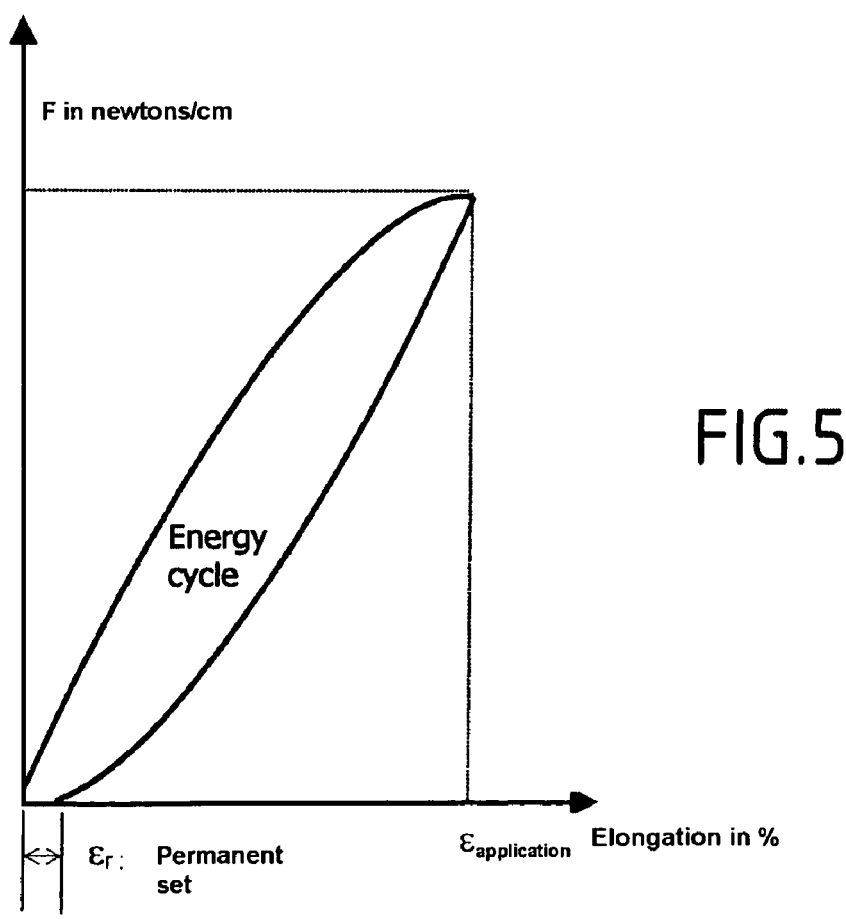
FIG. 5 illustrates the principle of the force-elongation tests and that of measuring the force and the tension set of a bandage for a given stretch.
Figure 6:
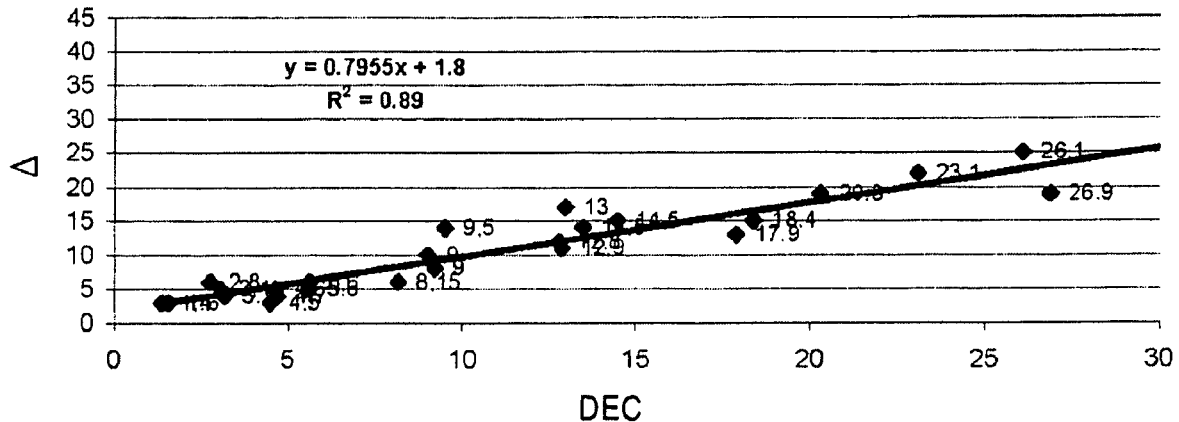
FIG. 6 illustrates the correlation between the pressure differences Δ, expressed in mm of mercury, and the dynamic elasticity coefficients, hereafter called DECs, expressed in newtons per cm, for all the individual bandages and compression systems produced according to the invention.
Figure 7:
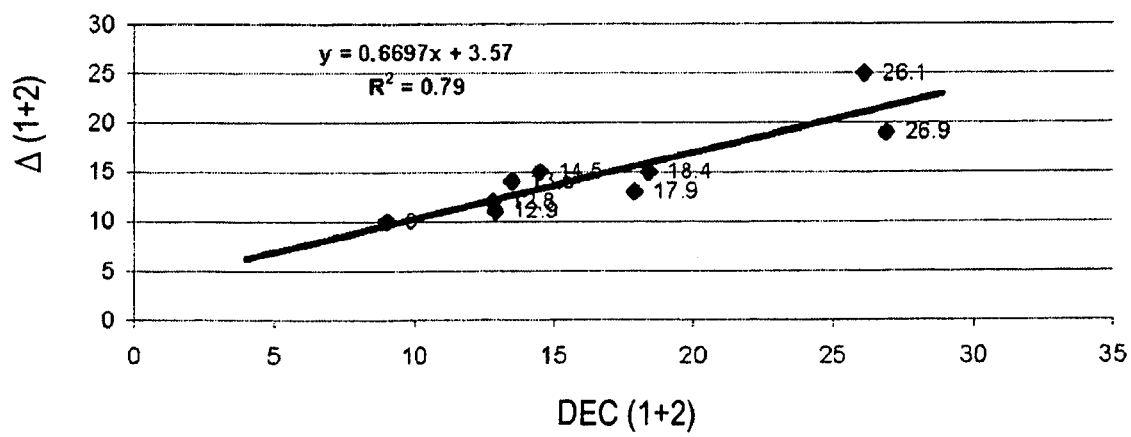
FIG. 7 illustrates the correlation between the same parameters, but only for the compression systems produced.
Figure 8:
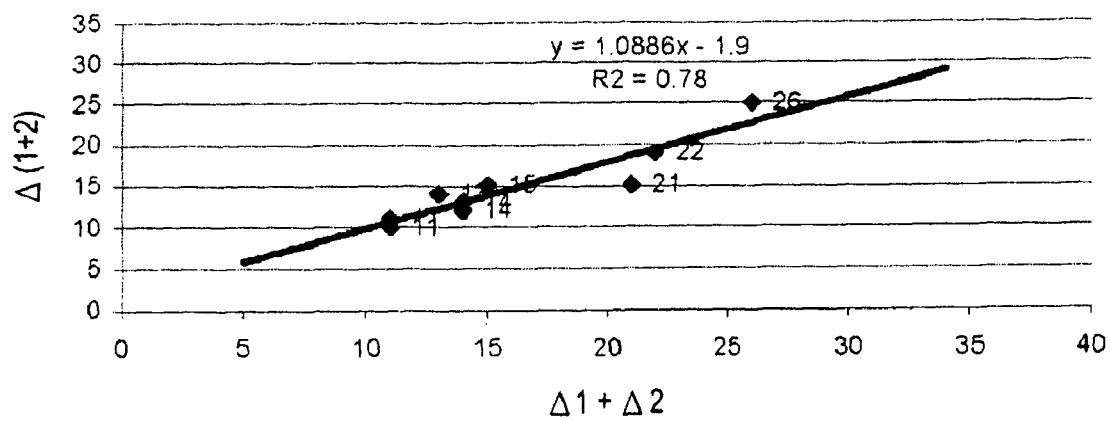
FIG. 8 illustrates the correlation between the sum of the pressure differences Δ for each individual bandage constituting a compression system and the pressure differences Δ for corresponding compression systems according to the invention.

Finally, the elastic properties of the bandages forming the layers of a compression system according to the present invention have been studied according to two other conventional tests, namely force-elongation curves and tension set. These two tests are illustrated in FIG. 5. Together with the basis weight, they also serve to characterize the products manufactured in the exemplary embodiments.

The test uses the same force-elongation testing machine (MTS brand dynamtensilometer) that was previously equipped with a 100 newton load cell.

An elastic bandage specimen of 20 cm length and 10 cm width is stretched to the elongation to which the force measurement at a rate of 100 mm per minute is intended to be carried out.

The test is carried out at a temperature of 21±2° C. and at 60±15% relative humidity.

The force at the target elongation, which is expressed in newtons per centimeter, is measured on the curve obtained.

The test principle of the tension set measurement will now be described.

This test uses the same tensile testing machine under the same conditions as previously.

The bandage is subjected to a load/unload cycle through to the desired stretch ($\epsilon_{application}$) of the bandage. Thus the tension set or permanent set $\epsilon_r$ is determined at the end of the cycle, as illustrated in FIG. 5.

This tension set, which is a stretch, is expressed as a percentage.

Various examples of compression systems according to the present invention will now be provided.

Different first layers that can be used in the compression systems of the present invention have been manufactured in the following manner:

1) Manufacture of the Padding

The padding is a nonwoven fabric manufactured by the conventional method of carding, lapping and preneedling from viscose fibres and polyester fibres in the proportion 60%:40% by weight.

These fibres have the following characteristics:
white viscose fibres without optical brightener of 1.7 dtex and 50 mm length; and
white polyester fibres without optical brightener of 3.3 dtex and 60 mm length.

This padding has a basis weight of 75 g per m².

The same padding has been used in association with various elastic bandages for the manufacture of first layers of the compression system according to the invention.

2) Manufacture of the Elastic Bandage a) To produce the first layer of compression systems according to the invention, different knits were used which were manufactured on a various 12-gauge Raschel knitting machine having the following technical characteristics:

Knit 1:
Warp:
Polyamide yarn marketed by the company Radici under the reference 78/24/1SZ;
feed: 48 yarns per 10 cm.
Bare elastane yarn marketed by the company Fillattice spa under the reference Linel 78 dtex;
feed: 48 yarns per 10 cm.
This yarn is subjected to a tensile stress of 8 cN for two yarns.
Weft:
Polyamide yarn marketed under the reference 78/24/1SZ; the weft insertion is 4.6.
Weft density: 9.3 wefts per cm.

Knit 2:
Warp:
Polyamide yarn reference 78/24/1SZ identical to the preceding;
feed: 48 yarns per 10 cm.
Elastane yarn reference Linel 78 dtex;
feed: 48 yarns per 10 cm.
This yarn is subjected to a stress of 8 cN for two yarns.
Weft:
Polyamide yarn reference 78/24/1SZ.
The weft insertion is 4.9.
Weft density: 9.3 wefts per cm.

Knit 3:
Warp:
Viscose yarn Nm 40;
feed: 49 yarns per 10 cm.
Elastane yarn reference Linel 78 dtex;
feed: 49 yarns per 10 cm.
This yarn is subjected to a stress of 12 cN for two yarns.
Weft:
Viscose yarn Nm 40.
The weft insertion is 3.7.
Weft density: 7.6 wefts per cm.

3) Manufacture of the First Layer by Needling

The general method of manufacture by needling is conventional.

The previously manufactured padding is unwound and inserted into the needle loom with one of the previously manufactured knits which is subjected to an extension of around 70 to 100%.

The needling is carried out with a needle board comprising 15000 needles for an overall width of 2.5 to 2.8 metres. At the output of the needle board a padding-knit assembly is obtained that is cut into overall widths of 10 cm that are wound without tension. These overall widths are then cut to give elastic bandages of the desired length that serve as the first layer in the compression system of the present invention.

The characteristics of the bandages obtained with the knits 1 to 3 are the following:

Example 1

| | |
|---|---|
| Basis weight | 230 g/m² |
| Force at 40% stretch | 1 newton/cm |
| Tension set | 4.4% |

Example 2

| | |
|---|---|
| Basis weight | 200 g/m² |
| Force at 50% stretch | 0.9 newtons/cm |
| Tension set | 7.1% |

Example 3

| | |
|---|---|
| Basis weight | 210 g/m² |
| Force at 40% stretch | 0.6 newtons/cm |
| Tension set | 4.5% |

4) Manufacture of the Third Layer

Various self-adhesive elastic bandages that can be used as the second layer of the compression system of the present invention were manufactured on a Tsudakoma® brand air jet loom.

During weaving a stress of around 30 cN per elastane yarn is applied.

After weaving, the product is fully shrunk by steaming.

A latex coating (with a product marketed by the company Sika France under the reference Sikacoll-2057/00) of around 30 g per m² of woven product is then applied in order to give the elastic bandage its self-adhesive character.

Bandages of 10 cm width are therefore produced. The technical characteristics of the different bandages thus produced are the following:

Example 4

Warp:
1/78 dtex Polyamide yarn
Polyamide air-jet covered elastane yarn marketed by the company Moulinages Schwarzenbach under the reference PE 635SEJ Weft:
Clear coloured acrylic yarn NM 34/1

| | |
|---|---|
| Weft density: | 10 wefts per cm |
| Basis weight: | 225 g/m² |
| Force at 50% stretch: | 0.5 newtons/cm |
| Tension set: | 4% |

Example 5

Warp:
2/78 dtex Polyamide yarn
Polyamide-covered elastane yarn marketed by the company Moulinages Schwarzenbach under the reference PE 9403NE Weft:
Clear coloured acrylic yarn NM 34/1

| | |
|---|---|
| Weft density: | 17 wefts per cm. |
| Basis weight: | 230 g/m² |
| Force at 50% stretch: | 1.5 newtons/cm |
| Tension set: | 3% |

Example 6

Warp:
2/78 dtex Polyamide yarn
Polyamide air-jet covered elastane yarn marketed by the company Moulinages Schwarzenbach under the reference PE 459SEJ Weft: Clear coloured acrylic yarn NM 34/1

| | |
|---|---|
| Weft density: | 10 wefts per cm |
| Basis weight: | 175 g/m² |
| Force at 80% stretch: | 4.3 newtons/cm |
| Tension set: | 23% |

Other commercially available self-adhesive elastic bandages have been used in the context of the present invention, the technical characteristics of which are the following:

Example 7

Self-adhesive elastic bandage marketed by the company Smith and Nephew in the four-layer Profore® system under the name Profore 4®.

Example 8

Self-adhesive elastic bandage marketed by the company Activa Healthcare under the name Actico®.

Example 9

Self-adhesive elastic bandage marketed by the company Urgo Ltd in the four-layer K4 system under the name Ko-flex®.

In order to illustrate the invention, the various bandages described in the examples 1 to 9 were combined to produce various compression systems according to the invention.

These combinations also allow the correlations that exist between the dynamic elasticity coefficient, abbreviated to DEC, and the pressure difference between resting pressure and working pressure to be demonstrated.

To do this, each of the bandages of the compression system is applied at a given extension and measurements are made, on application for each bandage and for each combination, of the DEC by tensile testing and of the pressure difference, hereafter called Δ, with the in vitro test apparatus.

The set of results obtained is gathered in Table I below, in which the first layer of the compression system according to the invention is referred to by the abbreviation C1, its DEC by DEC1 and its Δ by Δ1, and the second layer by the abbreviation C2, its DEC by DEC2 and its Δ by Δ2. Similarly, the abbreviation DEC1+DEC2 represents the sum of the DECs for each bandage, the abbreviation Δ1+Δ2 represents the sum of the pressure difference for each bandage, DEC (1+2) and Δ (1+2) respectively represent the results of DEC and pressure difference measurements carried out for the assembly of the two layers that form the compression system.

The percentage of elongation on application is specified for each bandage.

FIGS. 6 to 9 respectively illustrate the curves of the correlation between Δ and DEC for the assembly of individual bandages and their associations in the examples of the compression systems according to the invention (FIG. 6), between Δ and DEC only for the examples of compression systems according to the invention (FIG. 7), between the sum of the Δs for each individual bandage and the Δs measured for the examples of compression systems according to the invention (FIG. 8), and between the sum of the DECs for each bandage and the DECs measured for the examples of compression systems according to the invention (FIG. 9).

The set of these results demonstrates several important characteristics.

The variations in DEC and Δ for the same product shows the great variability between different batches of the same textile product. The DEC of example 4 thus varies, for the same 50% stretch, from 3.1 to 5.56. Similarly, in example 2, for the same 30% stretch, the DEC varies from 4.5 to 8.2. However, it has been observed that this great variability hardly affects the correlations existing between the various parameters studied.

In view of the curves represented in FIGS. 6 to 9 and the respectively obtained coefficients $R^2$ of 0.89, 0.79, 0.78 and 0.92, it is observed that despite all the parameters (textile variability, calibration, application, uncertainty in these measurements) excellent correlations are obtained. The DEC therefore allows the variability of textile materials to be factored out and hence constitutes a reliable parameter for characterizing compression systems according to the invention.

Finally, analysis of Table I shows that the classifications of short, medium or long stretch bandages generally used by health professionals and the manufacturers of support bandages do not cover, or only very partially cover, the reality and the possibility of using these products and in particular if their use in a dynamic system is considered. Thus it is seen from this table that it is possible to use the same bandage at very different stretch, for example 30 to 55% in the case of example 2. Similarly, the Actico bandage in example 8 is not used at its maximum stretch, as recommended in its use, but at 60%. This possibility of adapting bandages to treat pathologies is a novel and particularly advantageous element of the invention.

TABLE I

| C1 | C2 | DEC1 | DEC2 | DEC1 + DEC2 | DEC (1 + 2) | Δ1 | Δ2 | Δ1 + Δ2 | Δ (1 + 2) |
|---|---|---|---|---|---|---|---|---|---|
| EX3 40%+ | EX5 50% | 4.7 | 13 | 17.7 | 18.4 | 4 | 17 | 21 | 15 |
| EX1 40%+ | EX4 50% | 5.6 | 3.1 | 8.7 | 9 | 6 | 5 | 11 | 10 |
| EX2 30%+ | EX4 50% | 8.2 | 4.6 | 12.8 | 12.9 | 6 | 5 | 11 | 11 |
| EX2 40%+ | EX4 50% | 9.2 | 5.6 | 14.8 | 13.5 | 8 | 5 | 13 | 14 |
| EX2 50%+ | EX4 50% | 12.9 | 3.2 | 16.1 | 14.5 | 11 | 4 | 15 | 15 |
| EX2 55%+ | EX4 50% | 23.1 | 3.2 | 26.3 | 26.1 | 22 | 4 | 26 | 25 |
| EX2 50%+ | EX9 50% | 12.9 | 1.6 | 14.5 | 12.8 | 11 | 3 | 14 | 12 |
| EX2 50%+ | EX7 50% | 12.9 | 1.4 | 14.3 | 18.9 | 11 | 3 | 14 | 13 |
| EX2 30%+ | EX8 60% | 4.5 | 20.3 | 24.8 | 26.9 | 3 | 19 | 22 | 19 |

A good knowledge of the DEC for a bandage thus enables precise determination of its action, particularly in terms of the pressure difference, and consequently definition of the most appropriate pair of bandages to produce a compression system able to treat the patient effectively.

However, this is true only in the previously defined DEC region. This can be illustrated by the following counter example.

A compression system consisting of two layers corresponding to the examples 1 and 6 is produced and measurements of DEC and Δ are carried out according to the same methods as previously described for the modes of application corresponding to 30% stretch of the first layer (Example 1) and 90% of the second layer (Example 6).

The values of DEC and Δ for this system are the following:

| DEC 1 | DEC 2 | DEC 1 + DEC 2 | DEC (1 + 2) |
|---|---|---|---|
| 4.7 | 62.8 | 67.5 | 67.6 |

| Δ1 | Δ2 | Δ1 + Δ2 | Δ (1 + 2) |
|---|---|---|---|
| 6 | 63 | 69 | 52 |

In view of these results, it is observed that although there is indeed the correlation between the sum of the DECs and the DECs of the sum, there is conversely no correlation between the Δs of the sum and the sum of the Δs (69 against 52) outside the region claimed.

This confirms that if one of the two bandages has a DEC greater than 45 newtons/cm or if the assembly of the system has a DEC greater than 55 newtons/cm, it is not possible to predict the properties of the compression system and in particular the value of the pressure difference which is the key element in the effectiveness of the system. Although the exact reasons for this phenomenon are not precisely understood, it seems that if one of the two bandages is applied at too high a DEC, which is the case for Example 6 at 90%, it exerts too great a force, which leads to a large and immediate drop in pressure difference. In addition, if this drop continues over the course of time, it may lead to a loss of the compression system. Finally, the pressures applied may be dangerous because they are too high at the beginning.

This is demonstrated by the measurement of resting pressure, working pressure and the difference between said compression system and the bandage from Example 6 alone using the in vitro test apparatus.

The following results are thus obtained:
Example 6 at 90%

| | |
|---|---|
| Working pressure on application | 76 mm of mercury |
| Working pressure after one hour | 44 mm of mercury |
| Δ on application | 63 mm of mercury |
| Δ after one hour | 41 mm of mercury |

Example 1 at 30%+Example 6 at 90%

| | |
|---|---|
| Working pressure on application | 79 mm of mercury |
| Working pressure after one hour | 55 mm of mercury |
| Δ on application | 52 mm of mercury |
| Δ after one hour | 38 mm of mercury |

It can be seen that there is a very significant fall in pressure values from the first hour onwards.

In addition, there is also a risk of tourniquet with such a product. It is in fact observed that the working pressure values on application of around 80 mm of mercury are also very high. Applying a self-adhesive elastic bandage such as that of Example 6 at 90% will therefore be able to generate discomfort during the first hours, which can impair the observance by the patient who may quickly give up wearing such a system. It can also be noted that the pressure is applied to the model in vitro on an ankle of 35 cm diameter. For these systems are often applied to ankles having a mean diameter of 23 to 25 cm, such that the pressure applied will then be greater and the risks and the drawbacks previously mentioned will be increased. Finally, this bandage has a very high tension set of around 23%, it will therefore be very difficult to apply particularly when passing around the heel.

This decrease beyond one hour has been studied with the previously described in vitro test apparatus and the pressure differences are noted over several days in comparison with the commercial products Actico® and Profore® and with a compression system according to the invention consisting of the two following layers: Ex2-40%+Ex4-50%.

FIG. 10 illustrates the results obtained. It is observed that the two-layer system produced with the bandage of Example 6, which is beyond the fixed limits in terms of DEC according to the invention, exhibits a continuous reduction in pressure difference (curve 1). In addition, this pressure difference is very high to begin with, 52 mm instead of around 35 mm of mercury which is the upper value recommended for effectiveness.

Conversely, the two-layer system according to the invention (EX2-40%+EX4-50%) has an initial pressure difference that virtually does not change and remains constant in time (curve 3). It is comparable to the result obtained with the four-layer Profore® system (curve 4).

Conversely, it can be noted that the Actico® system (curve 2) also exhibits a drop in pressure difference, even if this is relatively low and seems to stabilize over the course of time. This product, which is applied at its maximum stretch, has an initial pressure difference of around 29 to 35 mm of mercury, which is acceptable, and this value stabilizes quickly in time. However, it has a tension set of around 11.5% at its maximum stretch which impairs its manipulation on application. As a result it is observed that the application of this bandage at its maximum stretch is difficult.

Finally, the importance for this product of the influence of the padding that is applied independently of the self-adhesive elastic bandage can also be noted by comparing the results of pressure differences between the elastic bandage applied alone and the bandage+padding assembly. When these two elements are tested on the in vitro test apparatus, applied at its maximum stretch, hereafter designated 100%, the following results are obtained:

|  | ACTICO alone 100% | ACTICO 100% + padding |
|---|---|---|
| Working pressure on application | 74 | 48 |
| Pressure after one hour | 56 | 40 |
| Pressure Δ on application | 47 | 29 |
| Δ after one hour | 41 | 26 |

Very significant variations are again observed which highlight the potential role of the padding.

All these results and these tests clearly demonstrate the advantage of compression systems according to the invention, which allow an effective product to be obtained with a pressure difference that is quickly stabilized and is stable over the course of time.

The choice of DEC in the defined range of values according to the invention also enables discomfort on application and the risks of tourniquet to be avoided.

Finally, even if the system may have a slight reduction in the pressure difference on application in the highest DEC values, the latter is low and remains within the limits that allows completely safe use of the product.

In addition, by choosing bandages that have a tension set less than 10% and preferably between 4 and 8%, a product that is easy to apply is always obtained, which is not evident in the case of products of the prior art of the Actico type.

The invention claimed is:

1. A Two-layer compression system that comprises:
   a first compression layer consisting of an elastic bandage linked over the whole of its surface with an absorbent layer and which has a dynamic elasticity coefficient of between 1 and 45 newtons/cm; and
   a second compression layer consisting of a self-adhesive elastic bandage that has a dynamic elasticity coefficient of between 1 and 45 newtons/cm;
   the dynamic elasticity coefficient of the compression system being between 5 and 55 newtons/cm.

2. The Two-layer compression system according to claim 1, wherein the dynamic elasticity coefficient of the system is between 10 and 35 and preferably between 15 and 30 newtons/cm.

3. The Two-layer compression system according to claim 1, wherein the first or the second layer has a dynamic elasticity coefficient of between 3 and 30.

4. The Two-layer compression system according to one of the claim 1, wherein the absorbent layer of the first layer consists of a woven or non-woven fibre-based textile material.

5. The Two-layer compression system according to claim 1, wherein the first layer consists of a padding linked by needling to a knit.

6. The Two-layer compression system according to claim 1, wherein the first or the second layer has a tension set, measured for their stretch on application, of less than 10%.

7. The Two-layer compression system according to claim 1, wherein at least one of the two layers incorporates a calibration means.

8. A Compression kit, that comprises a compression system according to claim 1 and a calibration system independent of the compression layers of the system.

9. A Compression kit, that comprises at least one absorbent first layer and several self-adhesive elastic bandages to produce a compression system according to claim 1.

10. Compression kit according to claim 9, which furthermore comprises a calibration system independent of the compression layers of the system.

11. The Two-layer compression system according to claim 1, wherein the first or the second layer has a tension set, measured for their stretch on application, of between 4 and 8%.

12. The Two-layer compression system according to claim 7, wherein said calibration means is in the form of pictograms.

13. The Compression kit according to claim 8, wherein said calibration system is a stencil or information to produce said stencil.

14. The Compression kit according to claim 10, wherein said calibration system is a stencil or information to produce said stencil.

15. A method of treating or preventing a venous disease condition by compression in a subject in need thereof, comprising applying to the subject the two-layer compression system of claim 1.

* * * * *